United States Patent
Doerr et al.

(10) Patent No.: US 7,894,476 B2
(45) Date of Patent: Feb. 22, 2011

(54) SYSTEM AND METHOD FOR MANAGING A DATA TRANSMISSION LAYER FOR A PERSONAL MEDICAL DEVICE

(75) Inventors: Thomas Doerr, Berlin (DE); Joachim Reinke, Berlin (DE)

(73) Assignee: Biotronik CRM Patent AG (CH)

( * ) Notice: Subject to any disclaimer, the term of this patent is extended or adjusted under 35 U.S.C. 154(b) by 163 days.

(21) Appl. No.: 12/139,708

(22) Filed: Jun. 16, 2008

(65) Prior Publication Data
US 2009/0028185 A1 Jan. 29, 2009

(30) Foreign Application Priority Data
Jul. 28, 2007 (DE) .................. 10 2007 035 533

(51) Int. Cl.
 *A61N 11/00* (2006.01)
 *H04J 3/06* (2006.01)
 *H04M 11/00* (2006.01)
(52) U.S. Cl. .................. 370/466; 379/106.02; 607/27
(58) Field of Classification Search .......... 370/465, 370/466, 467, 400, 401, 351, 352, 353, 356, 370/329, 328, 216, 217, 218; 607/27, 28, 607/29, 30, 31, 32, 60
See application file for complete search history.

(56) References Cited

U.S. PATENT DOCUMENTS

| | | | |
|---|---|---|---|
| 5,891,178 A | 4/1999 | Mann et al. | |
| 5,899,931 A | 5/1999 | Deschamp et al. | |
| 6,250,309 B1 | 6/2001 | Krichen et al. | |
| 6,386,882 B1 | 5/2002 | Linberg | |
| 6,442,432 B2* | 8/2002 | Lee | 607/59 |
| 6,907,291 B1* | 6/2005 | Snell et al. | 607/31 |
| 7,181,505 B2* | 2/2007 | Haller et al. | 709/219 |
| 7,389,144 B1* | 6/2008 | Osorio et al. | 607/29 |
| 7,440,805 B2* | 10/2008 | Holmquist et al. | 607/32 |
| 7,536,309 B1* | 5/2009 | Vasko et al. | 705/3 |
| 2007/0213600 A1* | 9/2007 | John et al. | 600/300 |

FOREIGN PATENT DOCUMENTS

| | | | |
|---|---|---|---|
| DE | 41 41 133 A1 | 5/1993 | |
| DE | 100 52 116 A1 | 5/2002 | |
| EP | 10 48 323 A2 | 11/2000 | |

* cited by examiner

*Primary Examiner*—Hanh Nguyen
(74) *Attorney, Agent, or Firm*—Craig A. Fieschko, Esq.; DeWitt Ross & Stevens S.C.

(57) ABSTRACT

A system (10) for managing data transmission for a medical device (20) has several data transmission protocols (15, 15', 15"), each having a differentiating designation (30). Each of several medical devices (20) have an identification (45) which identifies the medical device (20), and a data transmission interface (35) for data transmission from and to the medical device (20). A management unit (25) has a query unit (45) for the designation (30) of the data transmission protocol (15, 15', 15") of a medical device (20) on the basis of its identification (30), and a storage unit (50) for storing data transmission protocols (15, 15', 15"). The management unit (25) provides, on the basis of the designation query of an external device (55), a data transmission protocol (15, 15', 15") from the storage unit (50) which is compatible with the data transmission protocol (15, 15', 15") of the medical device (20).

25 Claims, 3 Drawing Sheets

SYSTEM AND METHOD FOR MANAGING A DATA TRANSMISSION LAYER FOR A PERSONAL MEDICAL DEVICE

FIELD OF THE INVENTION

The present invention relates to a system for managing a data transmission layer for a programmable personal medical device, in particular an implantable medical device such as a cardiac pacemaker, defibrillator, or the like, as well as a management unit for such a data transmission layer and a method for managing such a data transmission layer.

BACKGROUND OF THE INVENTION

Exchanging data for programming or managing programmable personal medical devices such as a cardiac pacemaker via data connections such as a line-based telephone network, the Internet, a radio-based telephone network, or similar means between a (central) service provider and the cardiac pacemaker is known. The data connections typically do not represent secure connections which are unconditionally trustworthy.

During operation of a cardiac pacemaker or defibrillator, data arises in regard to the medical device and in regard to its operation. This data results on one hand from the operating state of the personal medical device itself and on the other hand from data which is detected by the personal medical device. Such data is significant in particular for optimum aftercare. Such aftercare data which has been recorded by an implant may be transmitted via the above-mentioned connections to the service provider.

In the opposite direction, i.e., from the service provider to the implant, updates of the operating parameters or the operating program of the implant may be applied by the attending physician.

In both cases, on one hand for reasons of securing the private sphere and the confidentiality of the patient data and on the other hand for reasons of operational reliability and avoiding manipulations of the settings of the implant, predetermined protocols or modules are used in the data transmission, encryption and/or decryption and authentication algorithms being used in particular.

The encryption of a data transmission between a medical implant and a central service provider via POP is cited in U.S. Pat. No. 6,442,432.

Even if a data exchange does not occur via possibly unsecured data lines, but rather in a secure environment such as a hospital, an increase of the security may also be achieved by using appropriate protocols.

Experience has shown that algorithms or modules first classified as secure and adequate may be classified as unsecured or at least only restrictedly secure at a later time. In such a case, the problem arises that the protocols, algorithms, or modules must be easily replaceable both on the encrypting side and also on the decrypting side and/or on both sides of an authentication without the remainder of the data transmission or the useful data load having to be changed for this purpose.

The terms "algorithm", "module", and "protocol" are to be understood as fundamentally synonymous in the context of the present invention and are used interchangeably in the following discussion.

SUMMARY OF THE INVENTION

One object of the present invention is thus to perform a management of the data transmission layer, using which, for example, a remotely programmable medical device such as an implant (pacemaker or implantable cardiac defibrillator/ICD) receives new programming and transmits data, and simultaneously to ensure sufficient security of the data transmission layer and also a reliable and failsafe communication capability with the personal medical device.

This object is achieved according to the invention by a system for managing a data transmission layer for a programmable personal medical device, in particular an implantable medical device such as a cardiac pacemaker, defibrillator, or the like having the following components: a plurality of data transmission protocols, a plurality of programmable personal medical devices, and a management unit. Each data transmission protocol of the plurality of data transmission protocols has a designation, which is implemented to differentiate the data transmission protocol from at least one other data transmission protocol of the plurality of data transmission protocols. Each personal medical device of the plurality of personal medical devices has a programmable data transmission interface for a data transmission from and to the personal medical device using a data transmission protocol from the plurality of data transmission protocols, a control unit for changing the data transmission protocol of the programmable data transmission interface, and an identification. The control unit is at least implemented for the purpose of accepting a data transmission via the data transmission interface. The identification identifies the personal medical device. The management unit comprises a query unit for a query of the designation of the data transmission protocol of a personal medical device on the basis of the identification of the personal medical device and a storage unit for storing at least one data transmission protocol from the plurality of data transmission protocols. The management unit is also implemented to provide a data transmission protocol compatible with the data transmission protocol of the personal medical device from the memory unit on the basis of the designation query of an external device and/or to transmit a data transmission protocol determined on the basis of the designation query from the memory unit to the control unit of the personal medical device to change the data transmission protocol of the data transmission interface.

The object is also achieved by a management unit for managing a data transmission layer for a programmable personal medical device, in particular an implantable medical device such as a cardiac pacemaker, defibrillator, or the like, having a query unit and a storage unit. The query unit is implemented for a query of a designation of a data transmission protocol of a programmable data transmission interface of a personal medical device from a plurality of personal medical devices on the basis of an identification of the personal medical device. The designation is implemented to differentiate the data transmission protocol from at least one other data transmission protocol of a plurality of data transmission protocols. The storage unit is implemented to store at least one data transmission protocol from the plurality of data transmission protocols provided. The management unit is implemented according to the invention to provide a data transmission protocol compatible with the data transmission protocol of the personal medical device from the storage unit on the basis of the designation query of an external device and/or to transmit a data transmission protocol determined on the basis of the designation query from the storage unit to a control unit of the personal medical device to change the data transmission protocol of the data transmission interface.

Furthermore, the object is achieved by a method for managing a data transmission layer for a programmable personal medical device, in particular an implantable medical device such as a cardiac pacemaker, defibrillator, or the like, having the following method steps.

One method step comprises querying a designation of the data transmission protocol of a personal medical device of a plurality of personal medical devices on the basis of an identification of the personal medical device. The data transmission protocol is one of a plurality of data transmission protocols. Each data transmission protocol from the plurality of data transmission protocols is additionally provided with a designation, which is implemented to differentiate the data transmission protocol from at least one other data transmission protocol of the plurality of data transmission protocols.

A further method step comprises providing at least one data transmission protocol from the plurality of data transmission protocols, which is compatible with the data transmission protocol of the personal medical device or is provided for changing a data transmission protocol of a personal medical device.

The method according to the invention also has, as alternative or supplementary method steps: providing the data transmission protocol compatible with the data transmission protocol of the personal medical device on the basis of the designation query for an external device and/or transmitting a data transmission protocol determined on the basis of the designation query from the storage unit to the control unit of the personal medical device for changing the data transmission protocol of the data transmission interface.

The invention is based on the insight that a data transmission protocol which represents the data transmission layer in a software architecture may be replaced separately from the remaining software running in an implant, for example, only the data transmission protocol, but not necessarily also the remaining operation, experiencing a change. To be able to take this change, which is performed on the data transmission protocol, i.e., the mode of operation of the data transmission interface, of the personal medical device, into consideration during a further communication with the personal medical device, according to the invention, a query of the status of the data transmission interface and/or a designation of the current data transmission protocol which is used by the data transmission interface is performed, the further communication being performed while incorporating the result of this query. The management unit according to the invention is implemented for the purpose of selecting a matching data transmission protocol from the data transmission protocols stored in the storage unit and making it usable for a data exchange with the personal medical device on the basis of the feedback to the question about which data transmission protocol is currently used in the personal medical device.

In addition, the invention allows a data transmission protocol used in a personal medical device to be replaced or supplemented by another data transmission protocol, so that changes to the data transmission protocols used for the plurality of personal medical devices may be controlled and applied centrally by the management unit. On the basis of the check of which data transmission protocol is currently in a personal medical device, the management unit may select a data transmission protocol from the data transmission protocols stored in the storage unit and transmit it (have it transmitted) to the personal medical device, so that a specific data transmission protocol no longer seen as adequately secure may be replaced or supplemented by another in a targeted manner, for example.

The control unit of the personal medical device is set up for the purpose of being able to accept data via the data transmission interface, this data having been received by the data transmission interface according to the current data transmission protocol, for example. On the basis of this received data, the control unit is implemented for the purpose of performing a change to the data transmission protocol of the data transmission interface. Such a change may be an adaptation of individual parameters or also a complete replacement of the entire data transmission protocol, for example.

In order that different data transmission protocols may be differentiated from one another during the management of the data transmission layer, each of these data transmission protocols has a designation.

In one embodiment of the invention at least one personal medical device of the plurality of personal medical devices is an active medical implant. Special security requirements on the communication security, which are fulfilled by the present invention, exist in particular for an active medical implant.

In one embodiment of the invention, the personal medical device is an implantable cardiac pacemaker or defibrillator-cardioverter. Secure communication of programming data or detected cardiac data according to the invention, for example, is advantageous in particular during operation of a cardiac pacemaker or a defibrillator-cardioverter.

According to a further embodiment of the present invention, the plurality of data transmission protocols comprises encryption and decryption protocols as well as authentication protocols as the data transmission protocols. Encryption and decryption algorithms as well as modules for verifying a communication counterpart or intermediate station are particularly significant for secure and reliable data transmission. According to the invention, the data transmission protocols may also relate to other aspects of data transmission, however, such as compression of data or settings for feedback or receipts in regard to received data.

In one embodiment according to the invention, the plurality of data transmission protocols have first encryption and decryption protocols as well as authentication protocols for use in the data transmission interface of a personal medical device and second encryption and decryption protocols and authentication protocols for use during the provision by the management unit. With an asymmetrical structure of the data transmission protocols, an encryption module or protocol differs from the associated decryption protocol or module. This is correspondingly true for an authentication or verification of the particular communication participants. One data transmission protocol for the provision may be designed in such a manner that it is compatible, i.e., may successfully perform a data transmission, with a plurality of data transmission protocols which are used in different personal medical devices, while the corresponding data transmission protocols may each only establish or perform a successful communication with this one data transmission protocol and not with other protocols. A greater flexibility thus exists for the data transmission protocol to be provided and/or kept ready, without a reduction of the security occurring.

In one advantageous embodiment of the invention, the data transmission interface is provided with at least two data transmission protocols, in particular with a first protocol for encryption and a second protocol for decryption of a data transmission. The possibility thus exists of providing different protocols for the different communication directions, consideration also being able to be taken of the different computing capacities of the implant as the personal medical device and the external device for programming the implant, for example. Furthermore, a different data transmission protocol is provided for an incoming data transmission at the personal medical device, such as programming, than for an outgoing data transmission, such as aftercare data, a particular tailored compromise between speed and security being able to be set here.

According to a further embodiment of the invention, the designation comprises a version number, a creation date, an identification sign, and/or a classification of the data transmission protocol. A plurality of possible designations may be used for the purpose of making one data transmission protocol or one version of a data transmission protocol differentiable from another or another version, respectively. Version numbers are typically assigned upon the preparation of data transmission protocols built on one another and/or refined, which may provide a conclusion about the up-to-dateness of the protocol. This is similarly true for the assignment of the date on which the protocol was released, prepared, or used for the first time. An identification sign may be a label which was assigned independently of the version or class of the protocol for a specific instance of the protocol, this identification sign thus being especially for the protocol used in the personal medical device and differing from many or all other protocols. The identification sign may also be a label generated from the protocol itself, however, such as a hash value, which was generated on the protocol code. If such a label is retained and regularly checked, a check of the integrity of the protocol may additionally be provided.

According to a further embodiment of the invention, the query unit is implemented to query the designation from a data bank of the system on the basis of the identification of the personal medical device and/or to query the designation by querying the personal medical device, the personal medical device being implemented to respond to a query of the query unit by transmitting the designation. Maintaining an assignment of data transmission protocol and personal medical device via the designation and the identification in a databank may provide the matching data transmission protocol for a communication with a specific personal medical device (in particular a transmission to this device) using the correct protocol, without firstly a check or communication with the personal medical device itself having to be performed. This is advantageous in particular for an asynchronous transmission of data to the personal medical device. For example, if a program package is prepared for transmission to a personal medical device, this program package may be prepared directly after the databank query according to the data transmission protocol, for example, according to the matching encryption, and transmitted to the personal medical device. The transmission and the receipt may occur at different times from one another, the encrypted program package being buffered at an intermediate station (e.g., a patient intermediary device which is implemented for the relay to an implant), for example, until a possibility results for transmitting the program package to the personal medical device (e.g., when the implant enters the reception and transmission range of the patient intermediary device). The personal medical device now receives the encrypted program package and may use it directly without further coordination being necessary with the transmitter. As an alternative or supplement, however, a query of the system of the data transmission interface may also be directed directly to the personal medical device itself, which prompts the personal medical device to feedback, from which the designation of the particular current data transmission protocol may be inferred. In particular, a databank whose content is checked and verified by occasional or regular queries to the personal medical devices is advantageous.

According to an advantageous embodiment of the present invention, the storage unit is implemented for storing all data transmission protocols of the plurality of data transmission protocols. If the management unit is equipped with all possible data transmission protocols via the storage unit, it is thus ensured that a compatible data transmission protocol is provided for every data transmission protocol resulting upon the query.

According to a further advantageous embodiment, the management unit also has a programmable data transmission interface for data transmission from and to a personal medical device, which may be provided with a data transmission protocol compatible with the data transmission protocol of the personal medical device. The management unit is equipped with its own data transmission interface, using which a data transmission may be executed with (i.e., to and/or from) the personal medical device according to a data transmission protocol. In order that the management unit may communicate with all personal medical devices, the data transmission interface of the management unit is a designed in such a manner that at least one selected data transmission protocol matching with the particular personal medical device may be executed in each case therewith.

According to a preferred embodiment, the data transmission interfaces of management unit and personal medical device are implemented to use the data transmission protocol of the personal medical device, a data transmission protocol compatible therewith, and/or another, predetermined data transmission protocol during a transmission of a data transmission protocol to the control unit of the personal medical device. The transmission of the data transmission protocol to the personal medical device is performed either using and/or according to the data transmission protocol currently available in the personal medical device for general use, which is replaced or supplemented by the new data transmission protocol upon a successful transmission, or by a further data transmission protocol, preferably determined especially for this purpose.

According to one embodiment of the invention, a provision for which the management unit is implemented comprises a transmission of the compatible data transmission protocol to the external device and/or an acceptance and relay of the at least one data transmission from the external device to the personal medical device in accordance with the compatible data transmission protocol. The provision advantageously comprises an acceptance and relay of data transmissions from the external device to the personal medical device and from the personal medical device to the external device. One possibility according to the invention comprises the transfer of the data transmission protocol to the external device. The external device is thus itself equipped with the data transmission protocol. Another alternative or supplementary possibility comprises the management unit acting as a type of relay station between the external device and the personal medical device, the management unit ensuring that the communication with the personal medical device occurs according to the matching data transmission protocol.

In an advantageous embodiment, at least one patient intermediary device is provided for accepting and relaying data transmissions to and from at least one personal medical device. The patient intermediary device is designed in this case to receive the data transmission from the management unit and/or the external device, the received data being relayed in processed form or unchanged to the personal medical device. A corresponding measure is also provided for a transmission in the opposite direction.

According to a further embodiment of the invention, the management unit is implemented, upon provision of a new data transmission protocol in the storage unit, to transmit the new data transmission protocol to all control units or to control units selected on the basis of one or more predetermined criteria to change the data transmission protocol of the data transmission interfaces of the personal medical devices, the criterion or criteria particularly being selected from the group comprising identification of the personal medical device, type of the personal medical device, communication pathway to the personal medical device, designation of the data transmission protocol of the personal medical device, location of the personal medical device, and combinations thereof. Upon input of a new data transmission protocol into the storage unit of the management unit, the management unit is prompted to transmit this updated data transmission protocol—if it is provided—to personal medical devices for use in their data transmission interface. Therefore, upon an update of the storage unit, the personal medical device is preferably also equipped with updated versions automatically.

Criteria, on the basis of which the management unit is to decide whether and when a transmission is to occur to an implant, for example, as a personal medical device may be, for example:
- as soon as an implant reports for the purpose of data transmission, it is informed about the availability of a new encryption/decryption module and supplied therewith or
- all implants are immediately supplied with the new encryption/decryption module or
- specific implants are supplied with the new encryption/decryption modules according to serial numbers (number groups) or
- the implants are supplied with the new encryption/decryption module according to implant type,
- the provider via which the implant reports,
- the firmware status with which the implant reports,
- the region/country/licensing region,
- according to a list of the implants in which they are listed according to priority for an update,
- the type of the patient intermediary device via which the implant reports,
- the program in which the implant runs.

According to a further embodiment, the personal medical device is implemented to transmit a message to the management unit in the event of a performed and/or non-performed change of the data transmission protocol, the management unit being implemented to cause a corresponding databank entry. The personal medical device transmits a confirmation of a successfully performed update and/or change of the data transmission protocol and/or a message in regard to a failure during an update or change to the management unit in response to the transmission of a new data transmission protocol. In this manner, an incorrect entry is avoided in the databank, which may result if a corresponding entry was already performed in the databank, in which the assignment of personal medical devices and data transmission protocols is maintained, after transmission of the new data transmission protocol, without a confirmation of the completed adaptation of the personal medical device having been waited for.

According to one embodiment of the invention, the personal medical device is equipped with a further data transmission protocol from the plurality of data transmission protocols, which replaces the data transmission protocol of the personal medical device in the event of a breakdown thereof. The data transmission interface is equipped with at least two data transmission protocols or has access to these two protocols, one of the protocols being used for the purpose, as a further, predetermined protocol, of being employed in the case of a breakdown of the initially provided main protocol, for example. Such a breakdown may result due to a reset of the personal medical device, for example, in which the actually provided and preferred main protocol is lost.

Further advantageous designs of the invention result in particular by combination of features of the claims and from the following description of preferred exemplary embodiments.

The invention is explained in greater detail in the following on the basis of preferred exemplary embodiments with reference to the attached figures.

DETAILED DESCRIPTION OF PREFERRED VERSIONS OF THE INVENTION

Figure 1:
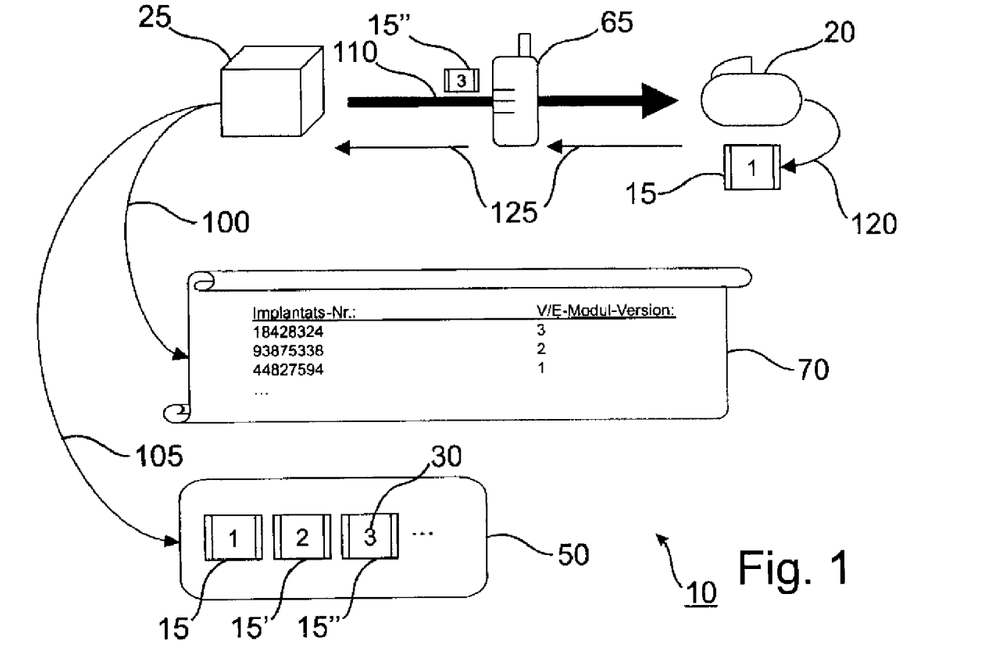
FIG. 1 shows a schematic illustration of a first aspect of an exemplary embodiment of the invention.

FIG. 1 shows a schematic illustration of a first aspect of an exemplary embodiment of the invention. The system 10 comprises a plurality of encryption and decryption modules 15, 15', 15" as data transmission protocols, a plurality of implants 20 as the personal medical device (only one implant 20 being shown in FIG. 1 for the sake of clarity), a patient intermediary device 65, a management unit 25, and a databank 70. The management unit 25 is equipped with a storage unit 50, which is situated outside the management unit 25 in the illustration of FIG. 1. The storage unit 50 contains a plurality of decryption and/or encryption modules 15, 15', 15", the modules 15, 15', and 15" each being provided with an index number 30 as a designation. The databank 70 contains an assignment of implant numbers for identifying the implants with the index numbers 30 or module version numbers of the modules 15, 15', 15". The management unit 25 has access in each case to the contents of the storage unit 50 and the databank 70.

Figure 2:
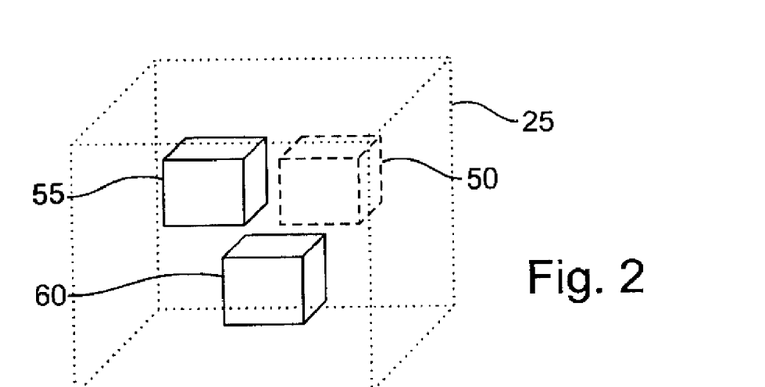
FIG. 2 shows a schematic view of the management unit from FIG. 1.

FIG. 2 shows a schematic view of the management unit 25 from FIG. 1. The management unit 25 (shown by dotted lines here) comprises a query unit 55 and a data transmission interface 60. In the illustration of FIG. 2, an alternative or supplementary possibility of the configuration of the storage unit 50 in comparison to the illustration in FIG. 1 is indicated using the dashed illustration of a storage unit 50 as a component of the management unit 25.

Figure 3:
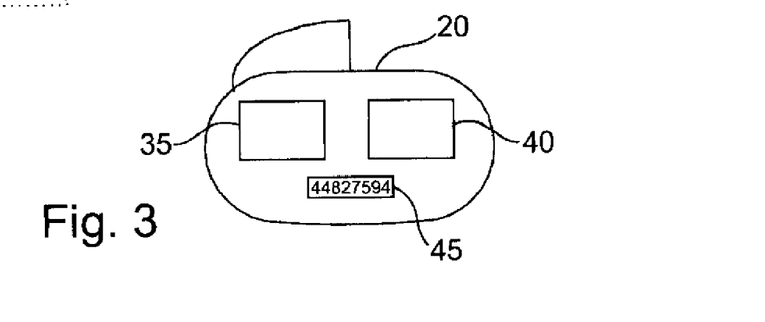
FIG. 3 shows a schematic view of the implant from FIG. 1.

FIG. 3 shows a schematic view of the implant from FIG. 1. The implant 20 comprises a data transmission interface 35, a control unit 40, and an identification 45 in the form of an implant number.

With reference to FIGS. 1 through 3, the management unit 25, which may also be referred to as a remote programming server here, establishes by a query of the databank 70 that the implant 20 uses an encryption/decryption module 15 having the index number (1). This query is indicated by the arrow 100 and occurs using the identification 45 of the implant 20. This module 15 does not represent the newest status, because a module 15" having a higher index number (3) is already available. The remote programming server 25 provides the newer module 15" from the storage unit 50, which may also be referred to as a (encryption/decryption module) repository here. This is indicated by the arrow 105. As indicated by the arrow 110, the remote programming server 25 transmits the module 15" to the implant 20, more precisely to the control unit 40 of the implant 20. The patient intermediary device 65 coordinated with the implant 20 functions as a relay station and relays the transmission from the remote programming server 25 to the implant 20. The implant 20, or again more precisely its control unit 40, sets up the programmable data transmission interface 35 using the new module 15" instead of the old module 15, which is indicated by the arrow 120. Depending on the result of this setup, the implant 20—again via patient intermediary device 65—reports about the successful (or also unsuccessful) transfer of the new module 15", which is indicated by the arrows 125.

Figure 4:
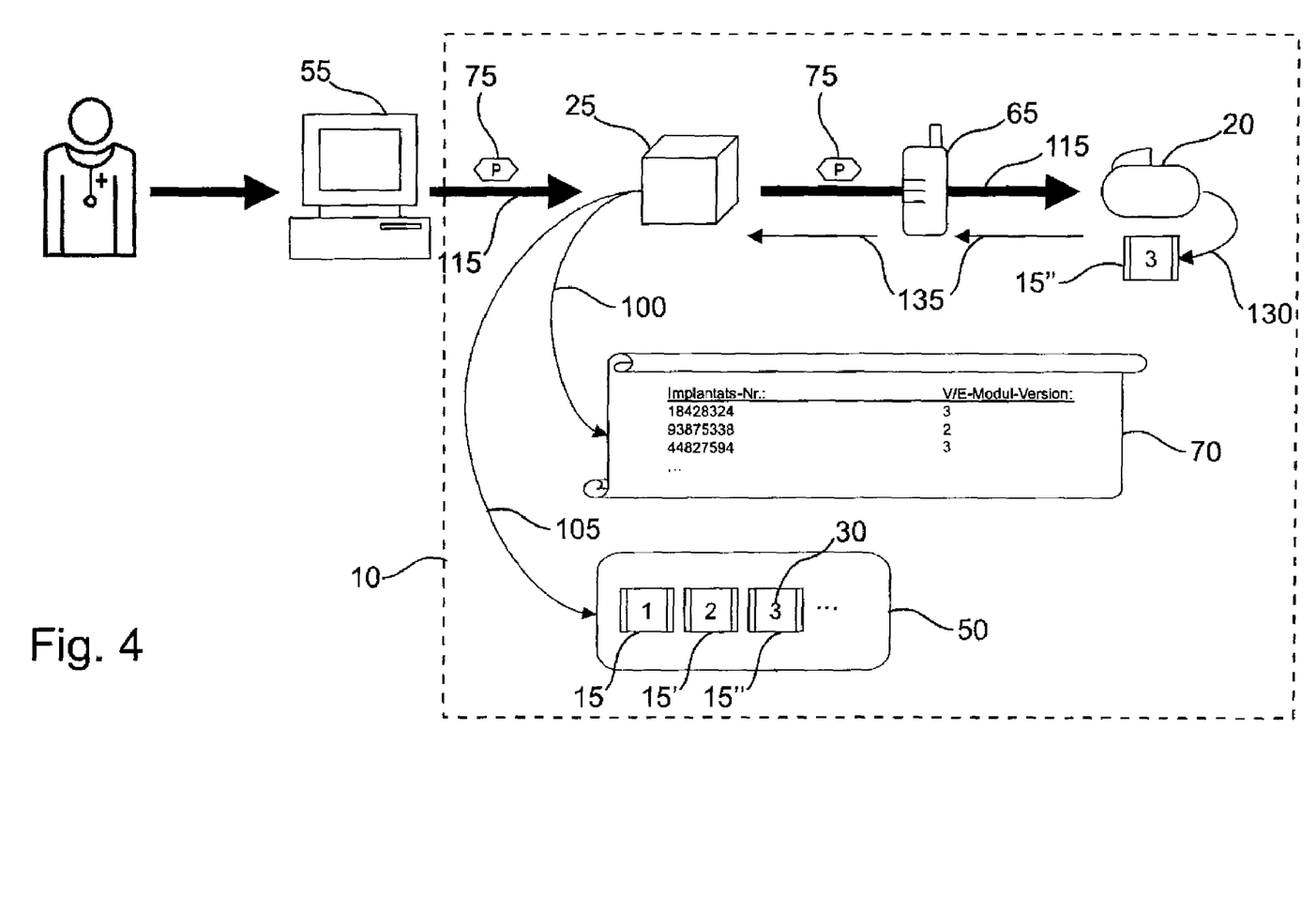
FIG. 4 shows a schematic illustration of a second aspect of an exemplary embodiment of the invention.

FIG. 4 shows a schematic illustration of a second aspect of an exemplary embodiment of the invention. The system 10 in the illustration of FIG. 4 essentially corresponds to the system shown in FIG. 1, the management unit 25 and the implant 20 also being shown in greater detail in FIGS. 2 and 3.

In FIG. 4, in addition to the system 10, a computer 55 is shown as an external device, to which a physician has access. The physician prepares a package 75 for reprogramming the implant 20 in the computer 55, for example, having an altered parameter set for operating the implant 20. The package 75 is transmitted to the remote programming server 25, which directs a query 100 of the module used by the intended implant 20 to the databank via its query unit 55. This query 100 has the result that the module 15" having the index number (3) is used. The remote programming server 25 acquires the module 15" from the memory and equips its data transmission interface 60 therewith, which performs an encryption of the package 75. The encrypted package 75 is transmitted by the remote programming server 25 via the patient intermediary device 65 to the implant 20. The implant 20 receives the package 75 using its data transmission interface 35 and decrypts it using its module 15" (indicated by arrow 130). Similarly to the sequence described above, the implant 20 confirms the successful (or also unsuccessful) transfer of the new program from the package 75 via the patient intermediary device 65 (indicated by arrows 135).

Figure 5:
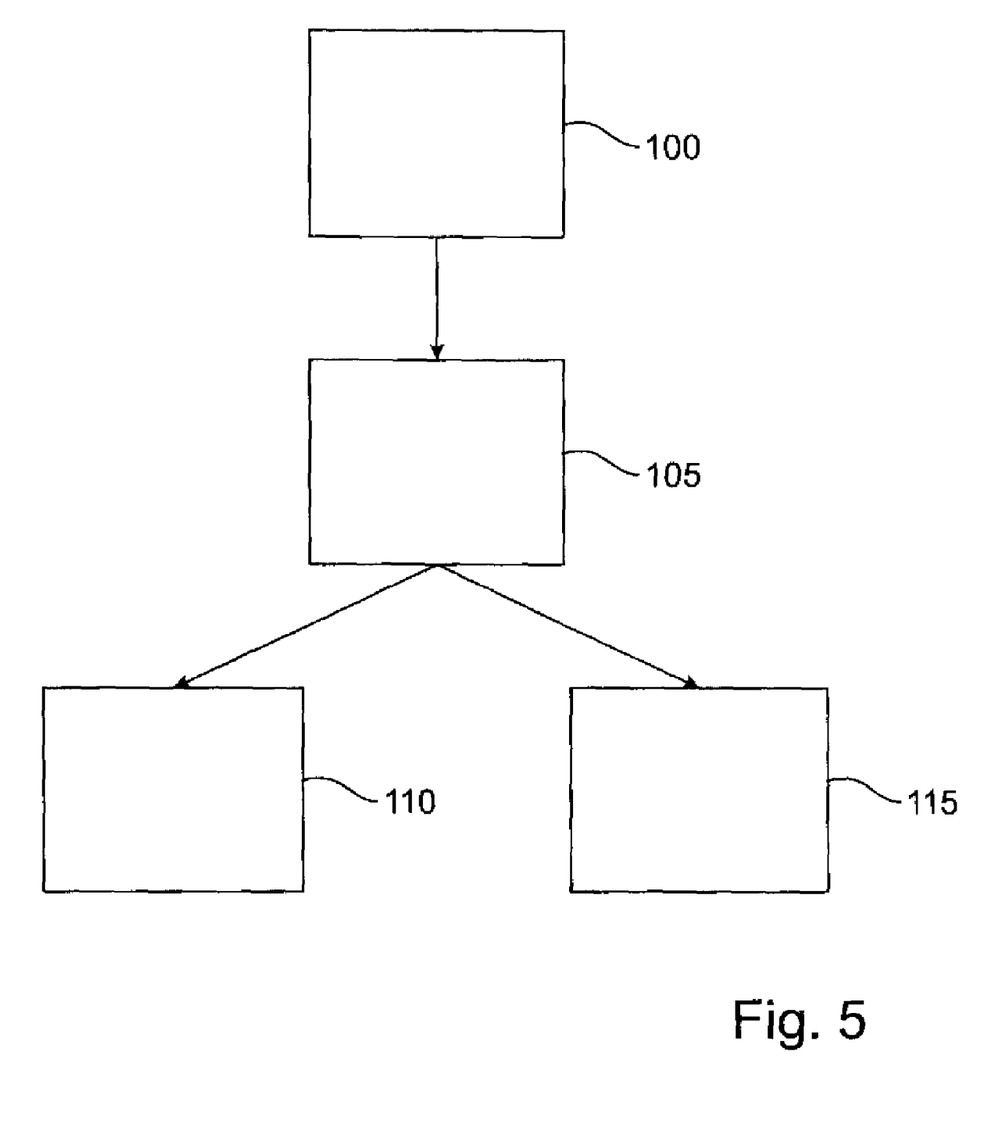
FIG. 5 shows a schematic illustration of a method sequence according to the invention.

FIG. 5 shows a schematic illustration of a method sequence according to the invention. In step 100, a query of a designation of a data transmission protocol of a personal medical device from a plurality of personal medical devices is performed on the basis of an identification of the personal medical device, the data transmission protocol belonging to a plurality of data transmission protocols and each data transmission protocol from the plurality of data transmission protocols being provided with a designation, which is implemented to differentiate the data transmission protocol from at least one other data transmission protocol of the plurality of data transmission protocols. In step 105, a provision of the at least one data transmission protocol from the plurality of data transmission protocols, which is compatible with the data transmission protocol of the personal medical device or is provided for changing a data transmission protocol of a personal medical device, is performed on the basis of step 100. In step 110, a transmission of a data transmission protocol determined on the basis of the designation query from the storage unit to the control unit of the personal medical device to change the data transmission protocol of the data transmission interface is performed, while as an alternative or a supplement thereto, a provision of the data transmission protocol compatible with the data transmission protocol of the personal medical device is performed on the basis of the designation query for an external device in step 115.

A further exemplary embodiment according to the invention comprises an application for a physician, who wishes to reprogram an implant, which he may execute on a commercially available computer (external device) of his selection. With the aid of this application, the physician compiles programming for the implant (personal medical device) and transmits it via a suitable data line (Internet, GPRS, GSM, UMTS, inter alia) to the remote programming server (management unit). The remote programming server comprises a repository (storage unit) for encryption/decryption modules (data transmission protocols), a list (databank), on which it is noted which implant currently communicates via which encryption/decryption module, and a device or interface for communicating with the physician application. The remote programming server has the capability of being able to encrypt an implant program with the aid of one of the encryption/decryption modules, and the capability of relaying an encrypted implant program via a suitable data line (Internet, GPRS, GSM, UMTS, inter alia) to a patient intermediary device in proximity to the implant, which is to be reprogrammed. The station device relays the reprogramming data package into the implant. The implant has a running implant program, according to which the therapies delivered to the patient by the implant are determined, an encryption/decryption module, via which received data may be decrypted (and data to be transmitted may be encrypted), and a device, which is implemented to check a decrypted implant program for validity.

In this exemplary embodiment, the components of the system work together as follows:

On one hand, an update of the encryption/decryption module may be provided in the implant. The remote programming server transfers a list about which implants currently contain which encryption/decryption module. As soon as a new pair of the encryption/decryption modules is stored in the repository in the remote programming server (the first part of the pair for use on the side of the remote programming server, the second part of the pair for use on the side of the implant), the remote programming server begins to relay it to all implants according to specific criteria, so that their encryption/decryption modules are brought to the newest state of the art. The implants checks the validity of a new encryption/decryption module upon receipt and then puts it into operation in each case. In addition, they inform the remote programming server using a suitable receipt either upon their next regular data transmission or immediately upon successfully putting the received encryption/decryption module into operation about the version of the encryption/decryption module currently used in the implant. The remote programming server notes this on its list (in the databank). If the implant (for example, upon a reset) changes back to a fallback program, which also contains a fallback encryption/decryption module, it informs the remote programming server in a suitable manner. This may again be performed either upon its next regular data transmission or immediately, so that a new attempt for the update may be performed if necessary.

On the other hand, a reprogramming of the implant may be provided. For this purpose, the remote programming server receives the task from the physician application of changing the programming of a specific implant. The remote programming server determines with the aid of the stored list which encryption/decryption module is currently used on the implant to be reprogrammed. The remote programming server encrypts the reprogramming package obtained from the physician application using the previously determined encryption/decryption module and transmits it (for example, via patient intermediary device) into the implant. The implant decrypts the reprogramming package and puts it into operation after checking for validity. In addition, the implant informs the remote programming server using a suitable receipt either upon its next regular data transmission or immediately upon successfully/unsuccessfully putting the new program into operation about the status of the reprogramming. If the implant changes back to a fallback program (for example, upon a reset), it informs the remote programming server about this in a suitable manner. This may again either occur upon its next regular data transmission or immediately.

What is claimed is:

1. A system (10) for managing data transmission for a programmable implantable personal medical device (20), the system including:
   a. a plurality of data transmission protocols (15, 15', 15"), each data transmission protocol (15, 15', 15") having a designation (30) which differentiates the data transmission protocol (15, 15', 15") from at least one other data transmission protocol (15, 15', 15") of the plurality of data transmission protocols (15, 15', 15"),
   b. a plurality of programmable personal medical devices (20), each programmable personal medical device (20) having:
      (1) a programmable data transmission interface (35) for a data transmission from and to the personal medical device (20) using one of the data transmission protocols (15, 15', 15") of the plurality of data transmission protocols (15, 15', 15"),
      (2) a control unit (40) for changing the data transmission protocol (15, 15', 15") of the programmable data transmission interface (35), the control unit (40) accepting a data transmission via the data transmission interface (35), and
      (3) an identification (45) which identifies the personal medical device (20),
   c. a management unit (25) having:
      (1) a query unit (55) for a designation query of the designation (30) of the data transmission protocol (15, 15', 15") of one of the personal medical devices (20) on the basis of the identification (45) of the personal medical device (20), and
      (2) a storage unit (50) for storing at least one data transmission protocol (15, 15', 15") of the plurality of data transmission protocols (15, 15', 15"), wherein the management unit (25):
      i. transmits a data transmission protocol (15, 15', 15") from the storage unit (50), on the basis of the designation query (100), to the control unit (40) of the personal medical device (20) to change the data transmission protocol (15, 15', 15") of the data transmission interface (35), and/or
      ii. provides a data transmission protocol (15, 15', 15") from the storage unit (50), on the basis of the designation query (100), to an external device (55), wherein the data transmission protocol (15, 15', 15") is compatible with the data transmission protocol (15, 15', 15") of the personal medical device (20).

2. The system (10) of claim 1 wherein at least one personal medical device (20) of the plurality of personal medical devices (20) is an active medical implant (20).

3. The system (10) of claim 2 wherein the personal medical device (20) is an implantable cardiac pacemaker (20) or defibrillator-cardioverter (20).

4. The system (10) of claim 1 wherein the plurality of data transmission protocols (15, 15', 15") includes:
   a. encryption and decryption protocols for encrypting and decrypting a data transmission, and
   b. authentication protocols for verifying the identity of a recipient of a data transmission.

5. The system (10) of claim 4 wherein the plurality of data transmission protocols (15, 15', 15") include:
   a. first encryption, decryption, and authentication protocols for use in the data transmission interface (35) of a personal medical device (20), and
   b. second encryption, decryption, and authentication protocols for use in the data transmission interface (35) of a personal medical device (20) upon provision by the management unit (25).

6. The system (10) of claim 1 wherein the data transmission interface (35) includes:
   a. a first protocol for encryption of a data transmission, and
   b. a second protocol for decryption of a data transmission.

7. The system (10) of claim 1 wherein the designation (30) includes at least one of a version number, a creation date, an identification sign, and/or a classification of the data transmission protocol.

8. The system (10) of claim 1 wherein the query unit (55) queries the designation (30):
   a. from a databank (70) of the system (10) on the basis of the identification (45) of the personal medical device (20), and/or
   b. by querying the personal medical device (20), the personal medical device (20) being implemented to respond to a query of the query unit (55) by transmitting the designation (30).

9. The system (10) of claim 1 wherein the storage unit (50) stores all data transmission protocols (15, 15', 15") of the plurality of data transmission protocols (15, 15', 15").

10. The system (10) of claim 1 wherein the management unit (25) also has a programmable data transmission interface (60) for data transmission from and to a personal medical device (20).

11. The system (10) of claim 10 wherein the programmable data transmission interface (60) is provided with a data transmission protocol (15, 15', 15") compatible with the data transmission protocol (15, 15', 15") of the personal medical device (20).

12. The system (10) of claim 1 wherein the data transmission interfaces (35, 60) of the management unit (25) and personal medical device (20) use:
   a. the data transmission protocol (15, 15', 15") of the personal medical device,
   b. a compatible data transmission protocol (15, 15', 15"), and/or
   c. another predetermined data transmission protocol (15, 15', 15"), during a transmission of a data transmission protocol to the control unit (40) of the personal medical device.

13. The system (10) of claim 1 wherein the management unit (25):
   a. transmits a compatible data transmission protocol (15, 15', 15") to an external device (55), and/or
   b. relays at least one data transmission between the external device (55) and the personal medical device (20) according to the compatible data transmission protocol (15, 15', 15").

14. The system (10) of claim 1 further including at least one patient intermediary device (65) for the acceptance and relay of data transmissions to and from at least one personal medical device (20).

15. The system (10) of claim 1 wherein the management unit (25), upon provision of a new data transmission protocol (15, 15', 15") in the storage unit (50), transmits the new data transmission protocol (15, 15', 15") to all control units (40).

16. The system (10) of claim 1 wherein the management unit (25), upon provision of a new data transmission protocol (15, 15', 15") in the storage unit (50), transmits the new data transmission protocol (15, 15', 15") to control units (40) selected on the basis of one or more predetermined criteria to change the data transmission protocol (15, 15', 15") of the data transmission interfaces (35) of the personal medical devices (20), the criteria including one or more of:
 a. identification (45) of the personal medical device (20),
 b. type of the personal medical device (20),
 c. communication pathway to the personal medical device (20),
 d. designation (30) of the data transmission protocol (15, 15', 15") of the personal medical device (20), and
 e. location of the personal medical device (20).

17. The system (10) of claim 1 wherein the personal medical device (20) transmits a message to the management unit (25) upon change of the data transmission protocol (15, 15', 15"), the management unit (25) causing a corresponding databank entry.

18. The system (10) of claim 1 wherein the personal medical device (20) is equipped with a further data transmission protocol (15, 15, 15") of the plurality of data transmission protocols (15, 15', 15"), which replaces the data transmission protocol (15, 15', 15") of the personal medical device (20) in the event of breakdown of the data transmission protocol (15, 15', 15").

19. A system (10) for managing data transmission for a programmable implantable personal medical device (20), the system including a management unit (25) having:
 a. a query unit (55) querying the designation (30) of a data transmission protocol (15, 15', 15") of a programmable data transmission interface (35) of a personal medical device (20) from a plurality of personal medical devices (20) on the basis of an identification (45) of the personal medical device (20), the designation (30) differentiating the data transmission protocol (15, 15', 15") from at least one other data transmission protocol (15, 15', 15") of a plurality of data transmission protocols (15, 15', 15"), and
 b. a storage unit (50) storing at least one data transmission protocol (15, 15', 15") of the plurality of data transmission protocols (15, 15', 15"),
wherein the management unit (25):
 (1) transmits a data transmission protocol (15, 15', 15") determined on the basis of the designation query from the storage unit (50) to a control unit (40) of the personal medical device (20) to change the data transmission protocol (15, 15', 15") of the data transmission interface (35), and/or
 (2) provides, on the basis of the designation query of an external device (55), a data transmission protocol (15, 15', 15") from the storage unit (50) compatible with the data transmission protocol (15, 15', 15") of the personal medical device (20).

20. A method for managing data transmission for a programmable implantable personal medical device (20), the method including the steps of:
 a. electronically querying (100) a designation (30) of the data transmission protocol (15, 15', 15") of a programmable implantable personal medical device (20) from a plurality of programmable implantable personal medical devices (20), wherein:
  (1) the designation (30) is queried on the basis of an identification (45) of the programmable implantable personal medical device (20),
  (2) the data transmission protocol (15, 15', 15") belongs to a plurality of data transmission protocols (15, 15', 15").
  (3) each data transmission protocol (15, 15', 15") of the plurality of data transmission protocols (15, 15', 15") is provided with a designation (30) which differentiates the data transmission protocol (15, 15', 15") from at least one other data transmission protocol (15, 15', 15") of the plurality of data transmission protocols (15, 15', 15"),
 b. electronically providing (105) at least one data transmission protocol (15, 15', 15") of the plurality of data transmission protocols (15, 15', 15") which:
  (1) is compatible, on the basis of the designation query (100) for an external device (55), with the data transmission protocol (15, 15', 15") of the programmable implantable personal medical device (20), or
  (2) is provided to a control unit (40) of the programmable implantable personal medical device (20) for changing a data transmission protocol (15, 15', 15") of the programmable implantable personal medical device (20).

21. A system for managing data transmission for a programmable cardiac therapy implant, the system including:
 b. several programmable cardiac therapy implants, each implant:
  (1) being associated with an identifying data label which uniquely identifies the implant,
  (2) having a data transmission interface configured to enable data transmissions from and to the implant, such data transmissions being defined in accordance with an enabled data transmission protocol identified by a version designation;
  (3) having a control unit configured to:
   i. accept data transmissions via the data transmission interface, and
   ii. revise the data transmission protocol of the data transmission interface,
 c. a management unit configured to:
  (1) store one or more of several data transmission protocols, each data transmission protocol being identified by a respective version designation;
  (2) query one of the implants having a specified identifying data label to determine the version designation of the implant's enabled data transmission protocol, and
  (3) send one of the stored data transmission protocols to the control unit of the implant having the specified identifying data label, with the sent data transmission protocol:
   i. having a version designation different from the version designation of the enabled data transmission protocol, and
   ii. becoming the enabled data transmission protocol defining the data transmissions of the implant's data transmission interface.

22. The system of claim 21:
 a. further including an external device separate from the implant, the external device being configured to accept data transmissions to be sent to the implant;
 b. wherein the management unit is also configured to send to the external device a data transmission protocol the same as, or compatible with, the data transmission protocol sent to and enabled within the control unit of the implant,
 whereby the external device can accept data transmissions to be sent to the implant, and send the data transmissions to the implant using the enabled data transmission protocol of the implant.

23. The system of claim 21 wherein the data transmission protocols are encryption and decryption protocols.

24. The system of claim 21 wherein the management unit, upon sending one of the stored data transmission protocols to the control unit of the implant having the specified identifying data label, also sends the same data transmission protocol to others of the several programmable cardiac therapy implants to become the enabled data transmission protocol therein.

25. The system of claim 21 wherein each implant is also configured to transmit a message to the management unit upon adopting a data transmission protocol sent by the management unit as the enabled data transmission protocol.

* * * * *